United States Patent [19]

Kawaguchi et al.

[11] 4,181,574
[45] Jan. 1, 1980

[54] **PRODUCTION OF ANTIBIOTICS BY FERMENTATION OF NOVEL STRAINS OF *MICROPOLYSPORA CAESIA***

[75] Inventors: Hiroshi Kawaguchi, Tokyo; Hiroshi Tsukiura, Mitaka; Koji Tomita, Kawasaki, all of Japan

[73] Assignee: Bristol-Myers Company, New York, N.Y.

[21] Appl. No.: 960,200

[22] Filed: Nov. 13, 1978

Related U.S. Application Data

[60] Division of Ser. No. 841,242, Oct. 11, 1977, which is a continuation-in-part of Ser. No. 815,329, Jul. 13, 1977, abandoned.

[51] Int. Cl.$^2$ ............................................. C12D 9/14
[52] U.S. Cl. ...................... 435/77; 435/85; 435/822; 435/119
[58] Field of Search ........................................... 195/96

[56] References Cited

PUBLICATIONS

DeBoer et al., Antibiotics Annual, 1955–1956, pp. 886–892.
Eble et al., Antibiotics Annual, 1955–1956, pp. 893–896.
Lewis et al., Antibiotics Annual, 1955–1956, pp. 897–902.
Meyer, The Journal of Antibiotics, Aug. 1971, pp. 558–560.
MacKellar et al., JACS 93, 4943–4945, Sep. 1971.
Duchamp et al., JACS 95, 4077–4078, Jun. 1973.
Reusser, Antimicrobial Agents & Chemotherapy, vol. 10, pp. 618–622, Oct. 1976.
Chemical Abstracts, vol. 85, 157884u (1976).
Gauze et al., Antibiotiki 22, 483–486 (1977).
Brazhnikova et al., Antibiotiki 22, 486–489 (1977).

*Primary Examiner*—Lionel M. Shapiro
*Attorney, Agent, or Firm*—Richard R. Lloyd

[57] ABSTRACT

A novel antibiotic complex designated herein as Bu-2313 is produced by fermentation of Micropolyspora sp. A.T.C.C. 31295, 31296, 31297 and 31298. The complex is separated into two bioactive components, Bu-2313A and Bu-2313B, which are structurally related to the streptolydigin-tirandamycin group of antibiotics. They are active against anaerobic bacteria.

7 Claims, 6 Drawing Figures

FIG. 4
INFRARED ABSORPTION SPECTRUM OF BU-2313B

FIG. 5
NMR SPECTRUM OF BU-2313A (60 MHz IN CDCl$_3$)

FIG. 6
NMR SPECTRUM OF BU-2313B (60 MHz IN $CDCl_3$)

PRODUCTION OF ANTIBIOTICS BY FERMENTATION OF NOVEL STRAINS OF *MICROPOLYSPORA CAESIA*

CROSS REFERENCE TO RELATED APPLICATIONS

This is a division of our co-pending application Ser. No. 841,242, filed Oct. 11, 1977, which in turn is a continuation-in-part of our prior co-pending application Ser. No. 815,329, filed July 13, 1977, and now abandoned.

SUMMARY OF THE INVENTION

This invention relates to novel antibiotic substances. More particularly, it relates to an antibiotic complex designated herein as Bu-2313, said complex being produced by cultivating a strain of *Micropolyspora caesia* having the identifying characteristics of A.T.C.C. No. 31295, 31296, 31297 or 31298 under submerged aerobic conditions in an aqueous medium until a substantial amount of Bu-2313 is produced in the culture medium and, optionally, recovering Bu-2313 from the culture medium.

This invention also provides two novel antibiotic components of Bu-2313, designated Bu-2313A and Bu-2313B, which are recovered from Bu-2313 complex by chromatographic procedures. Bu-2313 and its bioactive components Bu-2313A and Bu-2313B exhibit antibacterial activity against a variety of anaerobic bacteria and some aerobic bacteria. Bu-2313A and Bu-2313B are valuable in the treatment of infectious diseases in animals, including man, particularly diseases caused by anaerobic bacteria.

DESCRIPTION OF THE PRIOR ART

A series of three papers in Antibiotics Annual 1955-1956 describe biologic studies (page 886), isolation and characterization (page 893) and in vitro and in vivo laboratory studies (page 897) of streptolydigin, an antibiotic produced by fermentation of *Streptomyces lydicus*.

The Journal of Antibiotics, XXIV, 558 (1971) reports the isolation and characterization of tirandamycin, an antibiotic produced by fermentation of *Streptomyces tirandis*.

The Journal of the American Chemical Society, 93, 4943 (1971) reports the structure of tirandamycin.

The Journal of the American Chemical Society, 95, 4077 (1973) reports the complete stereochemical structures of tirandamycin and streptolydigin as determined by x-ray analysis.

Antimicrobial Agents and Chemotherapy—1976, page 618, reports that tirandamycin is an inhibitor of bacterial RNA polymerase in a manner similar to streptolydigin. It gives the structural formulae for streptolydigin and tirandamycin, as follows.

STREPTOLYDIGIN

TIRANDAMYCIN

Archives of Microbiology, 109, 65-74 (1976)[Chemical Abstracts, 85, 157884U (1976)] reports that *Streptomyces flaveolus*, strain Tu 1240 produces, in addition to tirandamycin, a closely related antibiotic designated as tirandamycin B. Tirandamycin B contains one more hydroxyl group than tirandamycin, and has the formula

DETAILED DESCRIPTION

Bu-2313 and its components Bu-2313A and Bu-2313B may be produced by fermentation of certain new chromogenic subspecies of *Micropolyspora caesia*. The structures of Bu-2313A and Bu-2313B are as follows:

Bu-2313A R = CH₃
Bu-2313B R = H

The Microorganism

In the course of screening for anti-anaerobic antibiotics, an oligosporic actinomycete strain No. E864-61 was isolated from a soil sample collected at Rajasthan District, India. It was isolated at 42° C. on an agar plate of beef extract-peptone-inorganic salts medium supplemented with 2 mcg./ml. of dihydroxymethylfuratrizine and 40 mcg./ml. of nystatin. Strain E864-61 was found to produce a new antibiotic complex Bu-2313 which is mainly active against various anaerobic bacteria.

Morphology

Strain E864-61 forms spores on the aerial and substrate mycelia. The majority of spores are borne singly either directly on the hyphae or on short sporophores. Paired spores and chains of two to eight spores are occasionally observed. The color of aerial mycelium is white, later turning to dull bluish green or light greyish green with abundant sporulation. Two types of pigment, violet and dark green, are produced in the agar medium. Spores are spherical to oval in shape, 0.5–0.7 by 0.5–1.2μ in size, and have smooth surface. The aerial hyphae occasionally twist in several to ten turns, which looks like a straight spore-chain. Fragmentation of substrate mycelium is generally not observed, while a variant withno aerial mycelium forms fragmented cells after a long period of incubation. The parent strain (S-2) is liable to give spontaneous variants which differ in the ability to form a greenish spore-mass, aerial mycelium and violet or green pigment. Properties of the original strain and some variants are shown in Table 1.

Table 1

| Strain No. | Greenish spore mass | Aerial mycelium | Pigment production Violet | Pigment production Green | Ratio of BU-2313A/ BU-2313B Produced |
|---|---|---|---|---|---|
| S-2 (original strain) | + | + | + | + | 8:2 |
| S-26 (variant) | + | + | − | − | 1:9 |
| S-7 (variant) | − | + | + | − | 6:4 |
| Y-29 (variant) | − | − | − | + | 1:9 |

Variant Y-29, produced from original strain S-2 by monospore isolation technique, was selected as a high producing strain. Cultures of actinomycete E864-61 strains S-2, S-26, S-7 and Y-29 have been deposited in the American Type Culture Collection, Washington, D.C., and added to its permanent collection of microorganisms as A.T.C.C. Nos. 31295, 31297, 31296 and 31298, respectively.

Cell Wall Composition

Strain E864-61 contains meso-DAP, galactose and rhamnose as diagnostic cell-wall components. The composition of the cell wall is shown in Table 2.

Table 2

| Amino Acid and Carbohydrate Composition of Cell Wall | |
|---|---|
| Amino Acid | Strain E864-61 |
| meso-DAP | +++ |
| LL-DAP | − |
| Glycine | − |
| Glutamic Acid | +++ |
| Alanine | +++ |
| Carbohydrate | |
| Arabinose | − |
| Galactose | +++ |
| Rhamnose | + |
| Mannose | TRACE |

Cultural Characteristics

Strain E864-61 grows vigorously on nutritionally rich media such as yeast extract-malt extract agar and Bennett's agar, while the growth is poor on chemically defined media such as starch-mineral salt agar, glucose-asparagine agar, tyrosine agar and glucose-ammonium salts agar. It gives no growth on Czapek's agar.

The original strain of E864-61 (S-2) forms abundant spores and aerial mycelium. It produces two types of pigment: reddish purple to reddish brown pigment on yeast extract-malt extract agar, peptone-yeast extract-iron agar and glucose-ammonium salts agar, and dark green pigment on oat meal agar, tyrosine agar and Bennett's agar. Variant No. S-26 sporulates well and forms aerial mycelium, but lacks the pigment-forming ability. Variant No. S-7 forms white aerial mycelium without greenish spore mass, and produces abundant reddish purple pigment but not the greenish pigment. Variant No. Y-29 lacks the ability to form spore-mass and aerial mycelium and hence shows a bacterium-like appearance. It produces only greenish pigment but this property is easily lost by transfer. The cultural characteristics of the original strain and spontaneous variants are shown in Table 3.

Table 3

Cultural Characteristics of Strain E864-61 and Variants

|   |   |   | Strain E864-61 No. S-2 | Variant No. S-26 | Variant No. S-7 | Variant No. Y-29 |
|---|---|---|---|---|---|---|
| 1. | Sucrose-nitrate agar (Czapek's agar) | G. VM | No growth. | No growth. | No growth, or growth of colonies. Dark rose. | No growth. |
|   |   | AM |   |   | Moderate. White. |   |
|   |   | D |   |   | None. |   |
| 2. | Yeast extract-malt extract agar (ISP No. 2) | G. VM | Moderate growth. Reddish brown. | Moderate growth Yellowish brown. | Moderate growth. Deep orange. | Moderate growth. Gold or olive green. |
|   |   | AM | Abundant. Dull bluish green. | Abundant. Dull yellow to light greyish green. | None or scant. White | None. |
|   |   | D | Light reddish brown. | Light reddish brown. | Deep reddish orange. | Gold or olive. |
| 3. | Oat meal agar (ISP No. 3) | G. VM | Moderate growth. Dark green. | Moderate growth. Light brown. | Moderate growth. Dull reddish purple. | Scant growth. Dull yellow. |
|   |   | AM | Abundant. Dull bluish green. | Scant. White and light greyish green. | None or scant. White. | None. |
|   |   | D | Light reddish brown. | None. | Dull reddish purple. | None. |
| 4. | Starch-mineral salts agar (ISP No. 4) | G. VM | Scant growth. | Scant growth. | Scant growth Light yellowish brown. | Scant growth. Colorless. |
|   |   | AM |   |   | None or scant. White. | None. |
|   |   | D |   |   | Pale purplish pink. | None. |
| 5. | Glucose-asparagine agar (ISP No. 5) | G. VM | Scant growth. | Scant growth | Scant growth. Orange. | Poor growth. Whitish. |
|   |   | AM |   | Scant. White | None. | None. |
|   |   | D |   | None. | None. | None. |
| 6. | Peptone-yeast extract iron agar (ISP No. 6) | G. VM | Poor growth. | Restricted Colorless. | Poor growth. Whitgrowth. Colorless | Poor growth. Whitish. |
|   |   | AM | None. | None. | None. | None. |
|   |   | D | Dull reddish purple. | None. | None. | None. |
| 7. | Tyrosin agar (ISP No. 7) | G. VM | Restricted growth. Olive green. | Poor growth. Pale yellowish pink. | Poor growth. Light yellowish brown. | Poor growth. Gold. |
|   |   | AM | Abundant. Pale bluish green. | Scant. White. | Scant. Pale yellow. | None. |
|   |   | D | None. | None. | Dull reddish purple. | None. |
| 8. | Glucose-ammonium salts agar | G. VM | Poor growth. Light yellowish brown to light reddish brown. | Scant growth. Light brown. | Scant growth. Light yellowish brown. | Scant growth. Gold to yellowish brown. |
|   |   | AM | Scant. White | Scant. White. | None. | None. |
|   |   | D | None. | None. | Deep reddish Purple. | None. |
| 9. | Bennett's agar | G. VM | Moderate growth. Dark green. | Poor growth. Colorless. | Moderate growth Deep orange. | Poor growth. Whitish |
|   |   | AM | Abundant. Light greyish green. | Scant. White and light greyish green. | None. | None. |
|   |   | D | Olive. | None. | Greyish pink. | None. |

Physiological Characteristics

Strain E864-61 is an aerobic and mesophilic actinomycete. The optimal growth temperature for the strain ranges from 32° C. to 42° C., and a moderate growth is obtained at 20° C. and 48° C. No growth is seen at 55° C. The physiological reactions and carbohydrate utilizations of the original and variant strains are shown in Tables 4 and 5 respectively.

Table 4

| | Physiological Reactions | | | |
|---|---|---|---|---|
| | Response | | | |
| Test | S-2 | S-26 | Y-29 | Method and Medium |
| Nitrite from nitrate in organic medium | − | + | − | Czapek's sucrose nitrate broth |
| Nitrite from nitrite in organic medium | − | − | − | 0.5% yeast extract, 1.0% glucose, 0.5% KNO$_3$, 0.1% CaCO$_3$ |
| Sodium chloride tolerance | Moderate growth at 4% NaCl or less concentration. No growth at 5% NaCl. | | | Basal medium: 1% yeast extract, 2% soluble starch, 1.5% agar |
| Casein hydrolysis in agar medium | ++ | ++ | − | Luedemann's agar medium |
| Reactions in skimmed milk solution | | | | |
| Coagulation | ++ | − | + | |
| Peptonization | + | − | − | |
| Gelatin liquefaction | ++ | + | − | 1.0% malt extract, 0.4% yeast extract, 0.4% glucose, 16% gelatin |
| H$_2$S production from L-cysteine | ++ | ++ | ++ | L-Cysteine (0.1%) added to tryptone yeast extract broth (ISP No. 1 medium) plus agar. H$_2$S detected with a paper strip containing 10% aq. lead acetate solution. |
| Hydrolysis of tyrosine | + | + | + | L-asparagine was omitted from the tyrosine agar. |
| Formation of melanoid | − | − | − | Tyrosine agar and peptone-yeast-iron agar |
| Catalase | ++ | ++ | ++ | Overnight growth on nutrient agar. Hydrogen peroxide solution. |
| Oxidase | − | − | − | Overnight growth on nutrient agar. Kovac's reagent. |
| Effect of temperature | Maximal growth at 32° to 42° C. Moderate growth at 20° C. and 48° C. No growth at 55° C. | | | Yeast extract-malt extract agar. |

Table 5

Carbohydrate Utilization of Strain E864-61

| | Original strain | Variant Nos. | | |
|---|---|---|---|---|
| | No. S-2 | S-26 | S-7 | Y-29 |
| 1. Glycerol | + | + | + | + |
| 2. D(−)-Arabinose | + | + | ± | + |
| 3. L(+)-Arabinose | + | + | + | + |
| 4. D-Xylose | + | + | + | + |
| 5. D-Ribose | + | + | + | + |
| 6. L-Rhamnose | + | + | − | + |
| 7. D-Glucose (positive control) | + | + | + | + |
| 8. D-Galactose | + | + | + | + |
| 9. D-Fructose | + | + | + | + |
| 10. D-Mannose | + | + | + | + |
| 11. L(−)-Sorbose | − | − | − | − |
| 12. Sucrose | − | − | − | − |
| 13. Lactose | + | + | + | − |
| 14. Cellobiose | + | + | + | + |
| 15. Melibiose | + | + | + | + |
| 16. Trehalose | ± | ± | + | + |
| 17. Raffinose | − | − | − | − |
| 18. D(+)-Melezitose | − | − | − | − |
| 19. Soluble starch | + | + | + | + |
| 20. Dulcitol | − | − | − | − |
| 21. Inositol | − | − | ± | + |
| 22. D-Mannitol | + | + | + | + |
| 23. D-Sorbitol | − | − | − | − |
| 24. Salicin | ± | − | − | − |
| 25. Cellulose | − | − | − | − |

Basal media: Luedemann basal medium
Cultural conditions: 37° C., 2 weeks

Taxonomy

The morphological characteristics and cell wall composition of strain E864-61 indicated that the organism should be classified in family Micromonosporaceae Krasilnikov 1938, described in Bergey's Manual of Determinative Bacteriology, 8th edition, 1975. When compared with the genera of Micromonosporaceae, strain E864-61 is differentiated from genus Micromonospora in its formation of aerial mycelium and its cell wall composition of Type IV although rhamnose is present instead of arabinose. It also differs from genera Thermoactinomyces, Actinobifida, Thermomonospora, Microbispora and Microtetraspora in the spore morphology and in the cell wall type (Type III for these genera).

Strain E864-61 is most related to genus Micropolyspora in the cell wall type, spore morphology and mode of sporulation. Eight species are described under genus Micropolyspora and a considerable diversity is seen among the species in the number of spores in a chain. Micropolyspora caesia is reported to have 1 to 5 spores and three species 5 to 20 spores in a chain. Strain E864-61 is similar to *Micropolyspora caesia* Kalakoutskii 1964 in that it forms predominantly single spores and occasionally chains of 2-8 spores. In addition, the strain resembles *M. caesia* in its color of aerial mycelium, range of growth-temperature and cell wall type, although it differs from the latter in the production of two kinds of diffusible pigment. Thus, strain E864-61 is considered to be a new chromogenic subspecies of *Micropolyspora caesia*.

Since strain E864-61 is easily mutatable naturally or artificially, it is to be understood that the present invention is not limited to original strain S-2 or variants S-26, S-7 or Y-29. It is specifically intended to include all Bu-2313-producing natural and artificial mutants and variants which can be produced from the described organisms by such means as X-radiation, ultraviolet radiation, treatment with nitrogen mustards, phage exposure, and the like. As with other antibiotics, it is anticipated that higher production of Bu-2313 may be achieved by the selection of highly productive strains after single colony selection, by treatment with various mutagens or by the genetic procedures of recombination, transformation or transduction.

Preparation of the Antibiotic

Antibiotic complex Bu-2313 is produced by culturing a strain of *Micropolyspora caesia* E864-61 (and preferably A.T.C.C. No. 31295, 31296, 31297, or 31298) under submerged aerobic conditions in an aqueous nutrient medium. The general procedures used for the culture of other actinomycetes are applicable to the cultivation of *Micropolyspora caesia* E864-61. The nutrient medium should contain one or more assimilable carbon sources such as glycerol, glucose, fructose, mannose, starch, dextrin, maltose, molasses, oils, fats and the like, either in purified or the crude state. The nutrient medium should also contain one or more assimilable nitrogen sources such as, for example, soybean meal, fish meal, malt extract, peptone, yeast extract, distiller's solubles, gluten meal, cornsteep liquor, cottonseed flour, casein, hydrolyzed protein substances, nitrates, ammonium salts, urea and the like. Nutrient inorganic salts such as sodium chloride, potassium phosphate, magnesium sulfate, calcium carbonate, and trace amounts of heavy metal salts such as copper, zinc, manganese, iron, and the like, may also be added to the medium. In the aerated submerged culture an antifoam such as liquid paraffin, soybean oil, fat or silicone may be utilized.

The fermentation temperature preferably should be in the range of from about 20° C. to about 48° C., and the most preferred range is from 32° C. to 42° C. The pH of the fermentation medium should be in the range of from about 5 to about 10, and the preferred range is from about 6 to about 8. Ordinarily, optimum production is obtained in 3-7 days. When tank fermentation is to be carried out, it is desirable to produce a vegetative inoculum in a nutrient broth by inoculating the broth culture with a slant or soil culture or a lyophilized culture of the organism. After obtaining an active inoculum in this manner, it is transferred aseptically to the fermentation tank medium. The antibotic activity in the fermentation broth may be determined by a paper disc-agar plate assay using *Bacteroides fragilis* as a test organism grown on GAM (Gifu anerobe medium, Nissui) under anaerobic conditions. After optimum broth potency has been obtained, the broth is filtered, preferably with filter aid. The mycelial cake is washed with water, and the combined filtrate and washings are adjusted to a pH of about 8 and passed through a column of nonionic macroreticular (macroporous) polymer resin such as Diaion HP-20 (Mitsubishi Chemical Industries) or Amberlite XAD-2 (Rohm and Haas Co.). The resin column is washed with water and aqueous methanol (e.g. 40% methanol) and is then eluted with about 95% aqueous methanol. The active fractions are combined, concentrated in vacuo, and evaporated or lyophilized to obtain the crude Bu-2313 complex. The crude solid thus obtained may be separated into its components, Bu-2313A and Bu-2313B, by chromatography on a macroreticular resin as indicated above and/or by silica gel chromatography.

When fermenting some strains of *Micropolyspora caesia* E864-61, it has been found that the addition of glycine to the fermentation medium (e.g., 1%) represses the production of Bu-2313A and gives Bu-2313B as the main product.

Physico-chemical Properties of Bu-2313A and Bu-2313B

Bu-2313A and Bu-2313B are both acidic substances isolated as pale yellow crystals. They are readily soluble in most organic solvents such as lower alcohols, ethyl acetate, chloroform and benzene, slightly soluble in hexane and alkaline water, but practically insoluble in water. They are stable in acidic solution but less so in alkaline solution, being inactivated at room temperature when held overnight in N/10 NaOH solution. Both components give positive reaction with ferric chloride but are negative in ninhydrin, anthrone, Sakaguchi and Tollen's reaction. Bu-2313A and Bu-2313B may be differentiated by two TLC systems as shown below:

| Component | Rf | |
|---|---|---|
| | System 1* | System 2** |
| Bu-2313A | 0.31 | 0.39 |
| Bu-2313B | 0.05 | 0.30 |

*Silica gel, chloroform - methanol (100:3)
**Silica gel, benzene - methanol (4:1)

Bu-2313A melts at 116°-118° C. and is optically active: $[\alpha]_D^{26} = -58°$ (c 0.5, MeOH). It shows a pKa' of 5.2 in 50% aqueous ethanol solution with a titration equivalent of 519 and its mass spectrum gave a molecular ion peak at m/e 517. Bu-2313B melts at 160°-162° C. and is optically active: $[\alpha]_D^{25} = -69.9°$ (c 0.3, MeOH) and $-34.9°$ (c 0.93, CHCl$_3$). It shows a pKa' of 4.9 in 46% aqueous ethanol solution with a titration equivalent of 509 and gave a molecular ion peak at m/e 503 in the mass spectrum.

Figure 1:
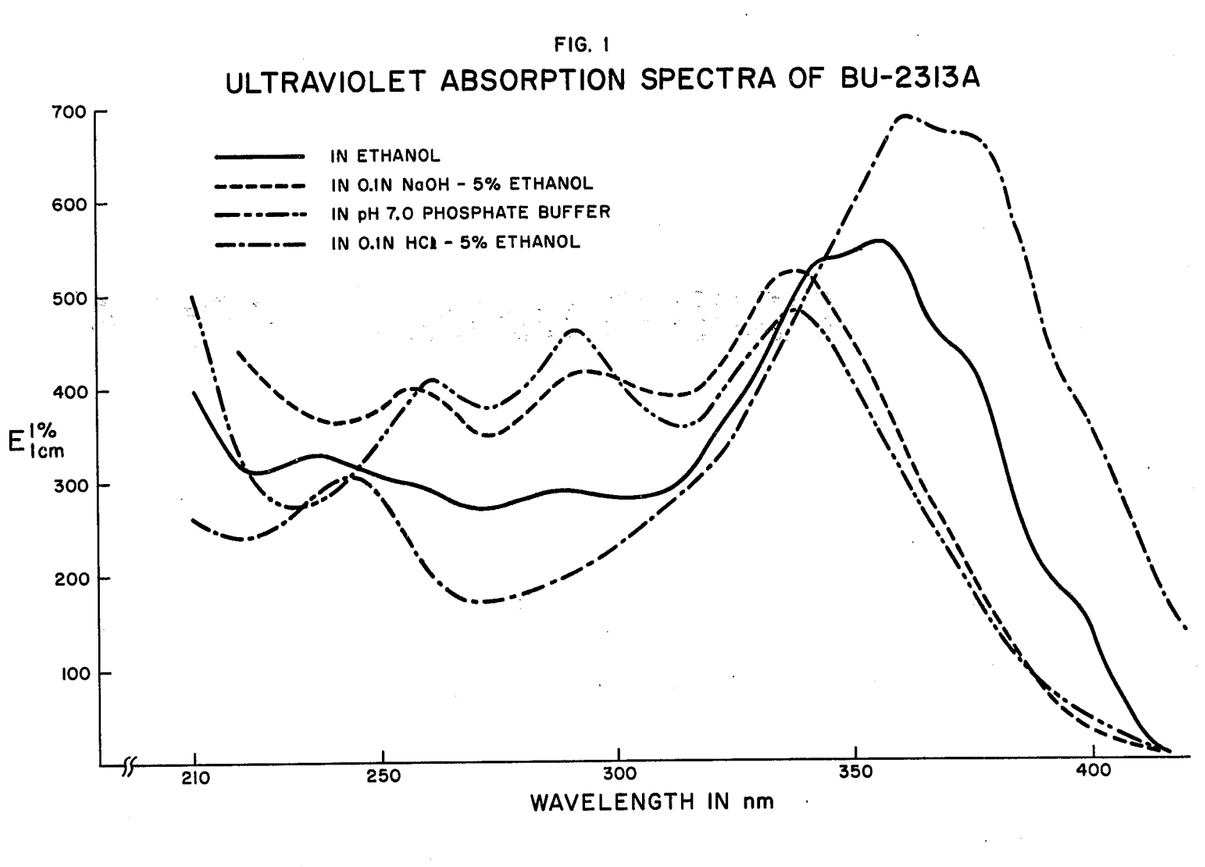
FIG. 1 shows the ultraviolet absorption spectra of Bu-2313A in ethanol, in N/10 NaOH-5% ethanol, in pH 7.0 phosphate buffer and in N/10 HCl-5% ethanol.
Figure 2:
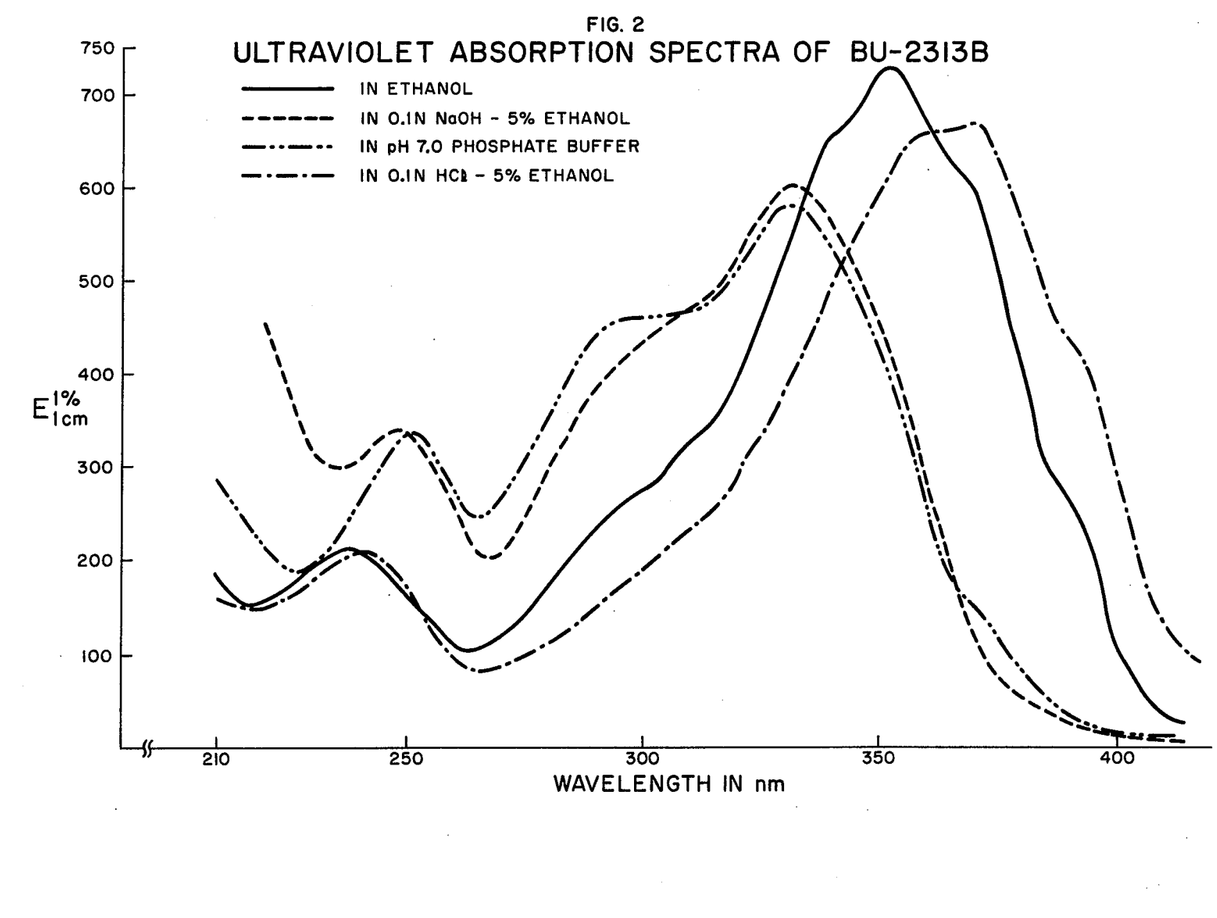
FIG. 2 shows the ultraviolet absorption spectra of Bu-2313B in ethanol, in N/10 NaOH-5% ethanol, in pH 7.0 phosphate buffer and in N/10 HCl-5% ethanol.

The ultraviolet spectra of Bu-2313A and Bu-2313B in various solvents are shown in FIGS. 1 and 2, respectively, and the absorption maxima are shown below:

| Solvent | Bu-2313A: $\lambda_{max}$ in nm ($E_{1cm}^{1\%}$) | | | |
|---|---|---|---|---|
| Ethanol | 235(330), | 288(290), | 344(535), | 355(555) |
| N/10 NaOH-5% Ethanol | 257(400), | 293(415), | 337(520) | |
| pH 7.0 Phosphate | | | | |

| | | | | |
|---|---|---|---|---|
| buffer | 261(418), | 291(430), | 339(482) | |
| N/10 HCl-5% Ethanol | 241(310), | | 361(690), | 373(670) |

| Solvent | Bu-2313B: $\lambda_{max}$ in nm ($E_{1cm}^{1\%}$) | | | |
|---|---|---|---|---|
| Ethanol | 239(220), | 295(260), | 352(730), | 368(610) |
| N/10 NaOH-5% Ethanol | 248(328), | 295(415), | 332(600) | |
| pH 7.0 Phosphate buffer | 251(335), | 294(454), | 332(580) | |
| N/10 HCl-5% Ethanol | 241(210), | | 359(656), | 370(665) | meningitiis meningitidis

Figure 3:
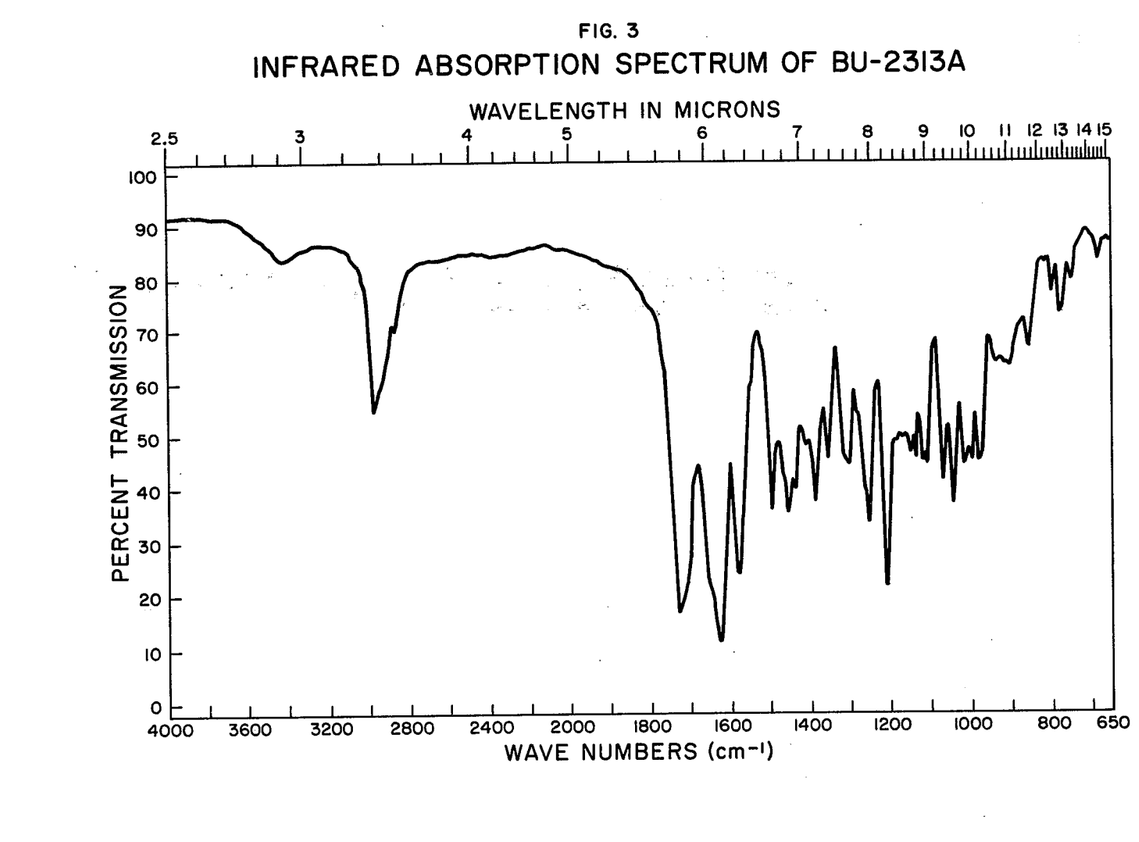
FIG. 3 shows the infrared absorption spectrum of Bu-2313A when pelleted in potassium bromide.
Figure 4:
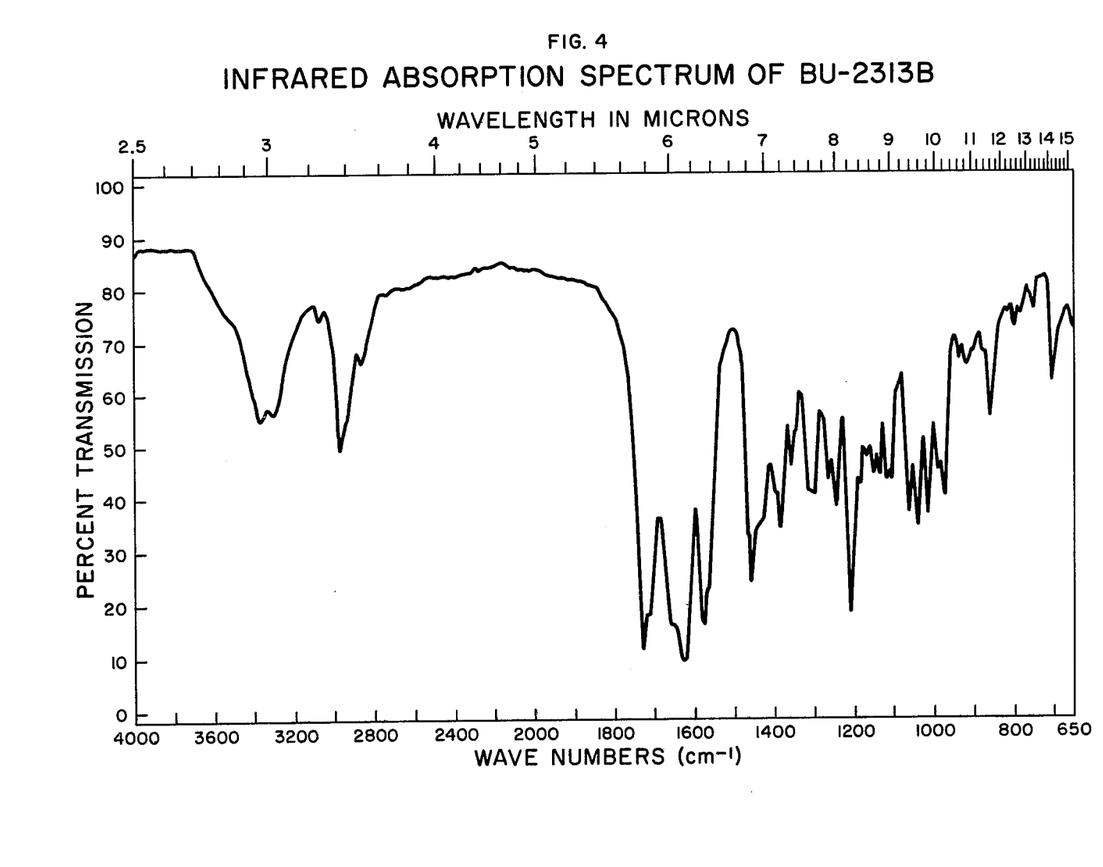
FIG. 4 shows the infrared absorption spectrum of Bu-2313B when pelleted in potassium bromide.
Figure 5:
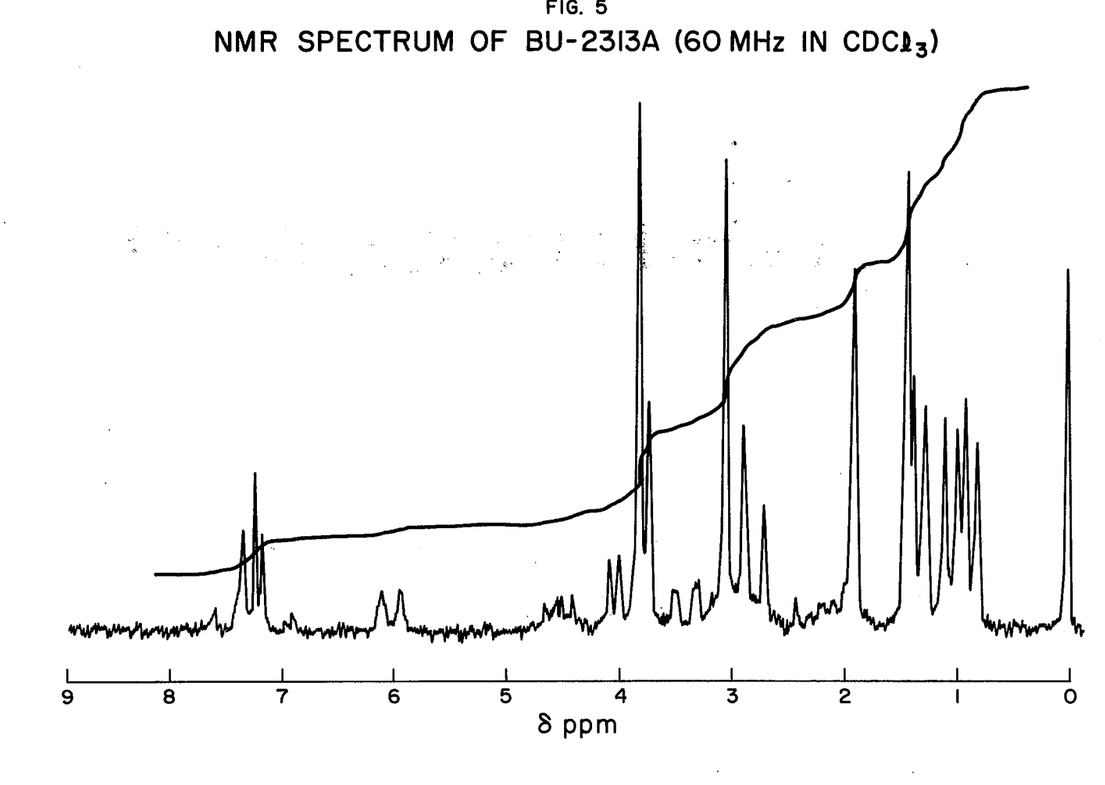
FIG. 5 shows the nuclear magnetic resonance spectrum of Bu-2313A in CDCl$_3$ (60 MHz).
Figure 6:
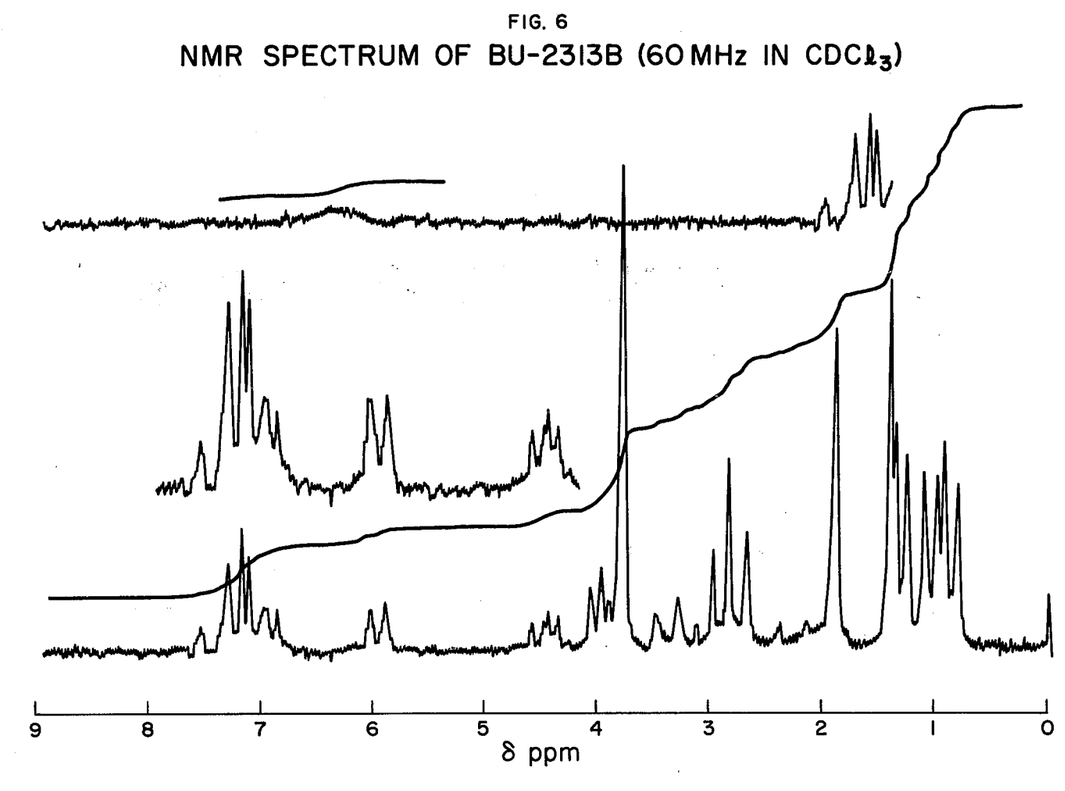
FIG. 6 shows the nuclear magnetic resonance spectrum of Bu-2313B in CDCl$_3$ (60 MHz).

The infrared spectra of Bu-2313A and Bu-2313B (in KBr pellet) are shown in FIGS. 3 and 4, respectively, and are very similar to each other with characteristic absorption bands observed at 1730, 1660, 1630, 1580 and 1210 cm$^{-1}$. A sharp band at 1500 cm$^{-1}$ is present in component A, while component B shows the characteristic N-H absorptions at 3200-3400 cm$^{-1}$ which are absent in component A. The proton NMR spectra of Bu-2313A and Bu-2313B (in CDCl$_3$) are shown in FIGS. 5 and 6, respectively, which indicate the presence of five C-methyl groups, one methyl ester group and a trans dienoic acid chromophore. The NMR spectrum of component A shows an N-methyl signal at $\delta$ 3.03 ppm which is absent in component B. The molecular ion peak was observed by mass spectroscopy for both Bu-2313A (m/e 517) and Bu2313B (m/e 503). Major fragment ion peaks are seen in the mass spectra at m/e 221 (base peak for component B), m/e 235 (base peak for component A) and m/e 283 (intense peak for both components A and B).

Bu-2313A and Bu-2313B are acidic substances and they, and their mixture, form salts with bases. As used herein, the term "nontoxic pharmaceutically acceptable salt" is intended to include their salts with metallic cations, e.g. alkali metal or alkaline earth metal cations such as sodium, potassium, calcium and magnesium.

Biological Properties of Bu-2313A and Bu-2313B

Antibacterial Spectrum

The minimum inhibitory concentration (MIC) of Bu-2313A and Bu-2313B were determined by the serial two-fold agar dilution method using a multi-inoculating apparatus against a variety of aerobic and anaerobic bacteria. Nutrient agar medium (Eiken) was generally used for aerobic bacteria, Gonococcus (GC) medium (Eiken) for fastidious aerobic organisms such as streptococci, Neisseria and Hemophilus species, and GAM agar medium (Nissui) for anaerobic bacteria.

The in vitro activities of Bu-2313A and Bu-2313B against various aerobic and anaerobic organisms are shown in Tables 6 and 7, respectively, along with those of tirandamycin and clindamycin which were used as reference compounds. Bu-2313A and Bu-2313B inhibited the growth of various anaerobic bacteria at low concentrations but showed only moderate to weak activity against many of the usual aerobic organisms such as *S. aureus*, *E. coli* and *K. pneumoniae*. However, strains of Bacillus species, streptococci, *Neisseria meningitidis*, *N. gonorrhoeae* and *Hemophilus influenzae* were susceptible to Bu-2313A and Bu-2313B. In general, the activity and antibacterial spectrum of Bu-2313A and Bu-2313B are very similar to those of tirandamycin, and the intrinsic in vitro activity of Bu-2313B seems to be somewhat higher than that of Bu-2313A.

Inoculum size effect

The influence of inoculum size on the MIC was tested for two anaerobic organisms (*B. fragilis* and *C. perfringens*) using GAM broth and agar medium. As shown in Table 8, the MICs of Bu-2213A and Bu-2313B were greatly affected by inoculum size when tested by the broth dilution method.

Bactericidal activity

The bactericidal potential of Bu-2313A and Bu-2313B was tested in two anaerobic and one aerobic organisms. Viable cell counts were made by plating a 0.1 ml aliquot of broth from every turbid-free tube after MIC determination. GAM agar plates were used for the viable cell count of *B. fragilis* and *C. perfringens* and Nutrient agar containing 5% horse serum for *S. pyogenes*, and the plates were incubated for 18 hours at 37° C. An antibiotic concentration allowing a growth of less than 100 colonies per plate was defined to be bactericidal (original inoculum size: $10^5$–$10^6$ cell/ml). As shown in Table 9, the antibacterial action of Bu-2313A and Bu-2313B seems to be bacteriostatic rather than bactericidal.

Table 6

| | | | MIC (mcg/ml) | | | |
|---|---|---|---|---|---|---|
| | | In vitro Activity Against Aerobic Bacteria | | | | |
| Code No. | Test organism | Test medium* | Bu-2313A | Bu-2313B | Tirandamycin | Clindamycin |
| Ec-3 | *Escherichia coli* Juhl A15119 | A | >100 | >100 | >100 | 12.5 |
| Ec-8 | *Escherichia coli* K-12 A9632 | A | >100 | >100 | meningitidis 100 | 25 |
| Kp-2 | *Klebsiella pneumoniae* A9678 | A | >meningitidis >100 | >100 | 100 | |
| Sm-1 | *Serratia marcescens* A20019 | A | >100 | >100 | >100 | 50 |
| Pa-13 | *Pseudomonas aeruginosa* A9843 | A | >100 | >100 | >100 | >100 |
| Pm-1 | *Proteus mirabilis* A9554 | A | >100 | >100 | >100 | 100 |
| Pg-1 | *Proteus morganii* A9553 | A | >100 | >100 | >100 | 100 |
| Sa-1 | *Staphylococcus aureus* 209P | A | 25 | 25 | 100 | 0.1 |
| Sa-2 | *Staphylococcus aereus* Smith | A | 12.5 | 12.5 | >100 | 0.1 |
| Sa-8 | *Staphylococcus aureus* #52-34 | A | 12.5 | 12.5 | 50 | 0.1 |
| Sl-1 | *Sarcina lutea* PCI-1001 | A | 25 | 12.5 | 50 | 0.025 |
| Mf-1 | *Micrococcus flavus* | A | 6.3 | 25 | 25 | 0.0125 |
| Bc-1 | *Bacillus cereus* ATCC 10702 A | A | 0.8 | 0.8 | 0.4 | 0.4 |
| Bs-1 | *Bacillus subtilis* PCI-219 | A | 1.6 | 1.6 | 3.1 | 0.8 |
| Sp-3 | *Streptococcus pyogenes* A9604 | B | 0.8 | 0.4 | 0.8 | 0.0125 |
| Sp-9 | *Streptococcus pyogenes* A20201 | B | 0.8 | 0.4 | 0.8 | 0.0125 |
| Sv-8 | *Streptococcus viridans* A21354 | B | 0.8 | 0.4 | 0.4 | 0.025 |
| Dp-4 | *Diplococcus pneumoniae* A9585 | B | 0.8 | 0.4 | 0.4 | 0.0125 |
| Nm-2 | *Neisseria meninigitidis* A20049 | B | 1.6 | 0.8 | 0.8 | 0.05 |
| Nm-4 | *Neisseria meninigitidis* A21496 | B | 3.1 | 1.6 | 0.8 | 0.025 |
| Ng-1 | *Neisseria gonorrhoeae* A15112 | B | 1.6 | 0.8 | 0.4 | 0.2 |
| Ng-4 | *Neisseria gonorrhoeae* A20154 | B | 0.8 | 0.8 | 0.4 | 0.2 |

Table 6-continued

| | | In vitro Activity Against Aerobic Bacteria | | | | |
|---|---|---|---|---|---|---|
| | | Test | MIC (mcg/ml) | | | |
| Code No. | Test organism | medium* | Bu-2313A | Bu-2313B | Tirandamycin | Clindamycin |
| Hi-3 | Hemophilus influenzae A9832 | B | 0.8 | 0.4 | 0.4 | 0.4 |
| Hi-7 | Hemophilus influenzae A20188 | B | 1.6 | 0.8 | 0.8 | 0.8 |

A : Nutrient agar (Eiken)
B : GC medium (Eiken)

Table 7

| | In vitro Activity Against Anaerobic Bacteria | | | | |
|---|---|---|---|---|---|
| | | MIC (mcg/ml) | | | |
| Code No. | Test organism | Bu-2313A | Bu-2313B | Tirandamycin | Clindamycin |
| Bf-1 | Bacteroides fragilis A20926 | 0.2 | 0.1 | 0.2 | 0.05 |
| Bf-3 | Bacteroides fragilis A20928-1 | 0.1 | 0.1 | 0.1 | 0.05 |
| Bf-4 | Bacteroides fragilis A20929 | 0.2 | 0.1 | 0.2 | 0.05 |
| Bf-6 | Bacteroides fragilis A20930 | 0.2 | 0.1 | 0.1 | 0.05 |
| Bf-7 | Bacteroides fragilis A20932 | 0.2 | 0.1 | 0.1 | 0.05 |
| Bf-10 | Bacteroides fragilis A20935 | 0.2 | 0.1 | 0.1 | 0.025 |
| Sm-1 | Sphaerophorus necrophorus A15202 | 0.2 | 0.1 | 0.1 | 0.025 |
| So-1 | Sphaerophorus pseudonecrophorus A20013 | 0.2 | 0.1 | 0.2 | 0.05 |
| Fo-1 | Fusobacterium mortiferum ATCC 9817 | 0.2 | 0.1 | 0.1 | 0.05 |
| Fv-1 | Fusobacterium varium ATCC 8501 | 0.1 | 0.1 | 0.1 | 0.05 |
| Ae-1 | Acidoaminococcus fermentans ATCC 25085 | 0.2 | 0.1 | 0.1 | 0.05 |
| Vp-1 | Veillonella parvula ATCC 17745 | 0.2 | 0.1 | 0.1 | 0.05 |
| Cb-1 | Clostridium acetobutylicum IAM 19011 | 0.4 | 0.2 | 0.2 | 0.1 |
| Cc-1 | Clostridium caproicum IAM 19228 | 0.4 | 0.2 | 0.2 | 0.1 |
| Ch-1 | Clostridium chavoei A9561 | 0.2 | 0.2 | 0.2 | 0.025 |
| Cp-1 | Clostridium perfringens A9635 | 0.4 | 0.2 | 0.1 | 0.025 |
| Cp-2 | Clostridium perfringens A21284 | 0.4 | 0.2 | 0.1 | 0.025 |
| Pp-1 | Peptocuccus prevotii ATCC 9321 | 0.2 | 0.1 | 0.2 | 0.1 |
| Pe-101 | Peptococcus aerogenes ATCC 14963 | 0.2 | 0.2 | 0.1 | 0.2 |
| Pb-1 | Peptostreptococcus anaerobius B43 | 0.4 | 0.4 | 0.2 | 0.8 |

Table 8

| | | Inoculum Size Effect | | | |
|---|---|---|---|---|---|
| | Inoculum | MIC (mcg/ml) in GAM agar | | | |
| | size cell/ml | Bu-2313A | Bu-2313-B | Tiranda-mycin | Clinda-mycin |
| B. fragilis A20928-1 | $1.2 \times 10^6$ | 0.1 | 0.05 | 0.2 | 0.025 |
| | $1.2 \times 10^7$ | 0.1 | 0.1 | 0.2 | 0.025 |
| C. perfringens A9635 | $7 \times 10^5$ | 0.1 | 0.1 | 0.8 | 0.0125 |
| | $7 \times 10^6$ | 0.1 | 0.1 | 0.8 | 0.0125 |
| | Inoculum | MIC (mcg/ml) in GAM broth | | | |
| | size cell/ml | Bu-2313A | Bu-2313B | Tiranda-mycin | Clinda-mycin |
| B. fragilis A20928-1 | $2.8 \times 10^6$ | 0.006 | 0.013 | 0.006 | 0.025 |
| | $2.8 \times 10^7$ | 0.8 | 0.4 | 0.2 | 0.05 |
| C. perfringens A9635 | $1.2 \times 10^5$ | 0.1 | 0.1 | 0.1 | 0.025 |
| | $1.2 \times 10^6$ | 100 | 25 | 12.5 | 12.5 |

Table 9

| | | Bactericidal Activity | | | | | | | |
|---|---|---|---|---|---|---|---|---|---|
| | | MIC & MBC (mcg/ml) | | | | | | | |
| | Inoculum size cell/ml | Bu-2313A | | Bu-2313B | | Tiranda-mycin | | Clinda-mycin | |
| | | MIC | MBC | MIC | MBC | MIC | MBC | MIC | MBC |
| B. fragilis A20928-1 | $2.8 \times 10^6$ | 0.03 | >0.8 | 0.006 | >0.8 | 0.025 | >0.8 | 0.05 | 0.4 |
| C. perfringens A9635 | $1.2 \times 10^5$ | 0.1 | 12.5 | 0.1 | 12.5 | 0.1 | 3.1 | 0.025 | 0.05 |
| So pyogenes A20201 | $6 \times 10^5$ | 0.4 | 12.5 | 0.2 | 12.5 | 0.4 | >12.5 | 0.05 | 6.3 |

Mouse Blood Levels

Blood levels were determined in mice following subcutaneous or oral administration of Bu-2313B (Na salt), clindamycin and Flagyl at graded dose levels (100, 50, 25 and 12.5 mg/kg). Blood samples were collected from orbital sinuses and assayed by paper disc-agar plate method using B. fragilis A20926 as the test organism. The results are shown in Table 10. The peak blood levels obtained with Bu-2313B were approximately 3-4 times higher than those of clindamycin by both parenteral and oral routes, while Flagyl showed better absorptions than Bu-2313B.

number of mice used in a group to obtain the mean score for each treatment and control group. Taking the mean score of the control group as a 100% infectivity level, the relative infection level was calculated for each

Table 10
Blood Levels In Mice

Subcutaneous administration

| Antibiotics | dose. | blood levels (mcg/ml) | | | |
|---|---|---|---|---|---|
| | | 15 min. | 30 min. | 1 hr. | 2 hr. |
| Bu-2313B | 100 mg/kg | 28 | 34 | 38 | 29 |
| | 50 | 25 | 27 | 20 | 9.3 |
| | 25 | 12 | 10 | 4.6 | 0.9 |
| | 12.5 | 4.4 | 1.7 | 0.4 | — |
| Clindamycin | 100 | 11 | 9.5 | 5.2 | 0.4 |
| | 50 | 7.0 | 5.8 | 3.4 | 0.3 |
| | 25 | 3.8 | 2.1 | 0.8 | 0.4 |
| | 12.5 | 1.9 | 1.2 | 0.5 | 0.3 |
| Flagyl | 100 | 98 | 121 | 98 | 40 |
| | 50 | 32 | 32 | 26 | 12 |
| | 25 | 16 | 15 | 12 | 8.3 |
| | 12.5 | 6.7 | 3.8 | 3.0 | — |

Oral administration

| Antibiotics | dose | blood levels (mcg/ml) | | | |
|---|---|---|---|---|---|
| | | 30 min. | 1 hr. | 3 hr. | 5 hr. |
| Bu-2313B | 100 mg/kg | 12 | 5.5 | 0.4 | 0.3 |
| | 50 | 3.0 | 0.7 | 0.2 | 0.1 |
| | 25 | 0.4 | 0.2 | 0.1 | — |
| | 12.5 | 0.3 | 0.2 | 0.1 | — |
| Clindamycin | 100 | 2.8 | 1.3 | 0.6 | — |
| | 50 | 0.9 | 0.5 | 0.3 | — |
| | 25 | 0.8 | 0.5 | 0.3 | — |
| | 12.5 | 0.6 | 0.4 | 0.3 | — |
| Flagyl | 100 | 56 | 41 | 24 | 13 |
| | 50 | 20 | 15 | 11 | — |
| | 25 | 8.8 | 6.7 | 6.1 | — |
| | 12.5 | 6.0 | 6.0 | 3.0 | — |

In vivo Activity

The effectiveness of Bu-2313A and Bu-2313B in vivo was tested in mice infected with *B. fragilis* A20926 (local), *C. perfringens* A9635 and *S. pyogenes* A20201 (systemic).

A localized infection of *B. fragilis* was established by subcutaneous injection into the dorsal neck of mice of 0.5 ml. of the bacterial suspension containing $2-5 \times 10^6$ cells plus 10 mg microcrystalline cellulose. Treatment was made subcutaneously or orally once daily for 5 days starting 30 minutes after the challenge. A group of five mice was used for each dosage level and the animals were dissected on the sixth day to measure the size of the subcutaneous abscess. Response in each animal was scored as 0-5 according to the size of the lesion, and the sum of the lesion scores was divided by the of the treatment groups and a $PD_{50}$ value was estimated by means of a log-probit plot. The results obtained with Bu-2313B are shown in Table 11 along with those of clindamycin and Flagyl. Clindamycin was more active than Bu-2313B or Flagyl in this infection model.

A systemic infection of *C. perfringens* or *S. pyogenes* was produced in mice by intraperitoneal challenge with a lethal dose of the pathogen in a 5% suspension of hog gastric mucin (American Laboratories). The antibiotic was administered subcutaneously or orally just before the bacterial challenge. The $PD_{50}$ was determined after 5 days. As shown in Table 12, Bu-2313B showed fairly good protection against these systemic infections by both subcutaneous and oral administration, while Bu-2313A was inactive by the oral route. Clindamycin was the most active in these in vivo tests.

Table 11
Localized Infection With *B. fragilis*

Subcutaneous treatment

| antibiotics | dose (mg/kg) | individual score | sum of score | mean score | infectivity level (%) | sc PD$_{50}$ |
|---|---|---|---|---|---|---|
| Bu-2313B Na salt | 50 × 5 | 0, 2, 3, 3, 3 | 11 | 2.2 | 52.4 | 60 mg/kg |
| | 12.5 × 5 | 2, 3, 3, 3, 3 | 14 | 2.8 | 66.7 | |
| | 3.1 × 5 | 3, 3, 3, 4, 4 | 17 | 3.4 | 81.0 | |
| | 0.8 × 5 | 4, 4, 4, 4, 4 | 20 | 4.0 | 95.2 | |
| Clindamycin | 50 × 5 | 0, 0, 1, 1, 2 | 4 | 0.8 | 19.0 | 2.8 mg/kg |
| | 12.5 × 5 | 1, 1, 1, 2, 2 | 7 | 1.4 | 33.3 | |
| | 3.1 × 5 | 2, 2, 2, 2, 2 | 10 | 2.0 | 47.6 | |
| | 0.8 × 5 | 4, 4, 4, 4, 4 | 20 | 4.0 | 95.2 | |
| Flagyl | 50 × 5 | 2, 2, 2, 2, 2 | 10 | 2.0 | 47.6 | 35 mg/kg |
| | 12.5 × 5 | 2, 2, 2, 3, 3 | 12 | 2.4 | 57.1 | |
| | 3.1 × 5 | 3, 3, 3, 4, 4 | 17 | 3.4 | 81.0 | |

Table 11-continued

| | | Localized Infection With B. fragilis | | | | |
|---|---|---|---|---|---|---|
| | 0.8 × 5 | 4, 4, 4, 4, 4 | 20 | 4.0 | 95.2 | |
| Control | | 4, 4, 4, 4, 5 | 21 | 4.2 | 100 | |

Oral treatment

| antibiotics | dose (mg/kg) | individual score | sum of score | mean score | infectivity level (%) | po PD$_{50}$ |
|---|---|---|---|---|---|---|
| Bu-2313B Na salt | 100 × 5 | 2, 2, 2, 3, 3 | 12 | 2.4 | 57.1 | ca 220 mg/kg |
| | 25 × 5 | 3, 3, 3, 3, 3 | 15 | 3.0 | 71.4 | |
| | 6.3 × 5 | 3, 3, 3, 4, 4 | 17 | 3.4 | 81.0 | |
| | 1.6 × 5 | 4, 4, 4, 4, 4 | 20 | 4.0 | 95.2 | |
| Clindamycin | 100 × 5 | 0, 0, 0, 1, 1 | 2 | 0.4 | 11 mg/kg | |
| | 25 × 5 | 1, 2, 2, 2, 2 | 9 | 1.8 | 42.9 | |
| | 6.3 × 5 | 2, 2, 3, 3, 3 | 13 | 2.6 | 61.9 | |
| | 1.6 × 5 | 4, 4, 4, 4, 4 | 20 | 4.0 | 95.2 | |
| Flagyl | 100 × 5 | 0, 1, 2, 2, 3 | 8 | 1.6 | 38.1 | 50mg/Kg |
| | 25 × 5 | 2, 2, 3, 3, 3 | 13 | 2.6 | 61.9 | |
| | 6.3 × 5 | 3, 3, 3, 4, 4 | 17 | 3.4 | 81.0 | |
| | 1.6 × 5 | 4, 4, 4, 4, 4 | 20 | 4.0 | 95.2 | |
| Control | | 4, 4, 4, 4, 5 | 21 | 4.2 | 100 | |

Table 12

Systemic Infection With C. Perfringens and S. Pyogenes

| | PD$_{50}$ (mg/kg) | | | |
|---|---|---|---|---|
| | C. perfringens | | S. pyogenes | |
| | sc | po | sc | po |
| Bu-2313A | 6.25 | NA at 50 | 7.6 | NA at 25 |
| Bu-2313B | 6.25 | 30 | 9 | 25 |
| Tirandamycin | 17 | 60 | 9.7 | 50 |
| Clindamycin | 0.08 | 0.22 | 0.3 | 2.1 |
| Flagyl | 31 | 60 | NT | NT |

NA : no activity
NT : not tested

Acute Toxicity

The acute LD$_{50}$'s of Bu-2313A and B were determined by subcutaneous, intraperitoneal and oral routes. Both the free acid and sodium salt forms of Bu-2313 were tested. The results are shown in Table 13. Bu-2313B showed significantly lower toxicity than Bu-2313A, which is interesting in view of only a slight structural difference between the two components (presence or absence of an N-methyl group).

Table 13

| Acute Toxicity | LD$_{50}$ (mg/kg) | | |
|---|---|---|---|
| | sc | ip | po |
| Bu-2313A (free acid) | 90 | 14 | 90 |
| Bu-2313A (Na salt) | 90 | 14 | — |
| Bu-2313B (free acid) | 225 | 115 | — |
| Bu-2313B (Na salt) | 200 | 55 | 280 |

One aspect of this invention relates to an antibiotic compound having the formula wherein R is H or CH$_3$, or a mixture thereof, or a nontoxic pharmaceutically acceptable salt thereof (and preferably the sodium salt).

Another aspect of this invention relates to the antibiotic compound, designated Bu-2313A, which is an acidic substance soluble in lower alcohols, ethyl acetate, chloroform and benzene, slightly soluble in hexane and alkaline water, but practically insoluble in water; which gives a positive reaction with ferric chloride but negative reactions with ninhydrin, anthrone, Sakaguchi and Tollen's reagents; and which in purified form melts at about 116°–118° C.; is optically active, having an $[\alpha]_D^{26}$ of about −58° (c 0.5, methanol); shows a pKa' of about 5.2 in 50% aqueous ethanol with a titration equivalent of 519; has a molecular ion peak at m/e 517 in its mass spectrum; has the empirical formula C$_{27}$H$_{35}$NO$_9$; and has the ultraviolet, infrared and nuclear magnetic resonance spectra substantially as shown in FIGS. 1, 3 and 5 of the drawings, respectively, or a nontoxic pharmaceutically acceptable salt thereof (and preferably the sodium salt).

Another aspect of this invention relates to the antibiotic compound, designated Bu-2313B which is an acidic substance soluble in lower alcohols, ethyl acetate, chloroform and benzene, slightly soluble in hexane and alkaline water, but practically insoluble in water; which gives a positive reaction with ferric chloride but negative reactions with ninhydrin, anthrone, Sakaguchi and Tollen's reagents; and which in purified form melts at about 160°–162° C.; is optically active, having an $[\alpha]_D^{25}$ of about −69.9° (c 0.3, methanol) and −34.9° (c 0.93, CHCl$_3$); shows a pKa' of about 4.9 in 46% aqueous ethanol with a titration equivalent of 509; has a molecular ion peak at m/e 503 in its mass spectrum; has the empirical formula C$_{26}$H$_{33}$NO$_9$; and has the ultraviolet, infrared and nuclear magnetic resonance spectra substantially as shown in FIGS. 2, 4 and 6 of the drawings, respectively, or a nontoxic pharmaceutically acceptable salt thereof (and preferably the sodium salt).

Another aspect of this invention relates to a microbiological process for the preparation of a mixture of the antibiotics Bu-2313A and Bu-2313B which comprises cultivating a strain of *Micropolyspora caesia* having the identifying characteristics of A.T.C.C. 31295, 31296 31297 or 31298 under submerged aerobic conditions in an aqueous culture medium containing assimilable sources of carbon and nitrogen until a substantial amount of said antibiotic mixture is produced by said microorganism in said culture medium. In a preferred embodiment the process includes the additional step of recovering the antibiotic mixture from the culture medium. In a more preferred embodiment, the microorganism is *Micropolyspora caesia* A.T.C.C. 31298.

Another aspect of this invention relates to a microbiological process for the preparation of the antibiotic Bu-2313B which comprises (a) cultivating a strain of *Micropolyspora caesia* having the identifying characteristics of A.T.C.C. 31295, 31296, 31297 or 31298 under submerged aerobic conditions in an aqueous culture medium containing assimilable sources of carbon and nitrogen until a substantial amount of antibiotic activity is produced by said microorganism in said culture medium; (b) recovering the antibiotic mixture produced in step (a) from the culture medium; and (c) separating Bu-2313B from said antibiotic mixture by chromatography on a macroreticular polymer resin. In a preferred embodiment the microorganism is *Micropolyspora caesia* A.T.C.C. 31298.

Another aspect of this invention relates to a microbiological process for the preparation of the antibiotic Bu-2313A which comprises (a) cultivating a strain of *Micropolyspora caesia* having the identifying characteristic of A.T.C.C. 31295, 31296, 31297 or 31298 under submerged aerobic conditions in an aqueous culture medium containing assimilable source of carbon and nitrogen until a substantial amount of antibiotic activity is produced by said microorganism in said culture medium; (b) recovering the antibiotic mixture produced in step (a) from the culture medium; (c) separating the major portion of Bu-2313B from said antibitoic mixture by chromatography on a macroreticular polymer resin; and (d) separating Bu-2313A from the residual Bu-2313B by chromatography on silica gel. In a preferred embodiment the microorganism is *Micropolyspora caesia* A.T.C.C. 31298.

The antibiotic compounds of the present invention include Bu-2313 complex, its components Bu-2313A and Bu-2313B, and salts and mixtures thereof. The invention includes within its scope pharmaceutical compositions containing at least one of such antibiotic substances mentioned above with a compatible pharmaceutically acceptable carrier. The compositions may also contain other active antibacterial agents. The compositions may be made up in any pharmaceutical form appropriate for the route of administration in question. Examples of such compositions include solid compositions for oral administration such as tablets, capsules, pills, powders and granules, liquid compositions for oral administration such as solutions, suspensions, syrups and elixers and preparations for parenteral administration such as sterile solutions, suspensions or emulsions.

As with other antibiotics, the dosage regimen for Bu-2313A or B will depend on the weight, age and general health of the patient, as well as the nature of the disease, and is within the discretion of the physician. In general, the oral dose will be in the range of 50–750 mg. of Bu-2313A or B (or mixture thereof), given 3–4 times per day.

The invention is illustrated by the following Examples, but is in no way limited thereby.

EXAMPLE 1

Preparation of Seed Culture and Small Scale Shake Flask Fermentation

A well-grown agar slant culture of the Bu-2313 producing organism, strain E864-61 No. Y-29, was used to inoculate 100 ml of liquid vegetative medium in a 500 ml. Erlenmeyer flask, which contained the following ingredients: 3% glucose, 3% soybean meal, 1% corn steep liquor and 0.5% CaCO$_3$. The media pH was adjusted to 7.0 before sterilization. The seed culture was incubated at 34° C. for 3 days on a rotary shaker (250 rpm) and 2–3 ml of the culture was transferred to a 500-ml Erlenmeyer flask containing 100 ml of fermentation medium composed of 3% sucrose, 3% linseed meal, 0.3% (NH$_4$)$_2$SO$_4$, 0.003% ZnSO$_4$.7H$_2$O and 0.5% CaCO$_3$. Antibiotic production reached a maximum after 4–7 days shaking at 28° C. The broth pH gradually rose with the progress of fermentation and reached 8.1–8.8 when the antibiotic potency of 150 mcg/ml was produced. The antibiotic activity in the fermentation broth was determined by a paper disc-agar plate method using *Bacteroides fragilis* as a test organism grown on GAM agar plates under anaerobic conditions.

EXAMPLE 2

Large Scale Tank Fermentation

A seed culture (110 liters) prepared from a well grown agar slant culture of strain E864-61 No. Y-29 was inoculated to 1500 liters of fermentation medium containing 3% glucose, 3% soybean meal, 1% corn steep liquor and 0.5% CaCO$_3$, in a 2500 liter tank. The fermentation was conducted at 31° C. with stirring at 200 rpm and an aeration rate of 1000 liters/minute. After 72 hours, the pH of the fermentation broth reached 8.2 and the antibiotic potency assayed 265 mcg./ml.

EXAMPLE 3

Isolation and Purification

A fermentation broth (1500 liters, assaying 200 mcg./ml.) was filtered with filter aid and the mycelial cake was washed with water. The filtrate was combined with the wash, adjusted to pH 8.3 and applied to a column of macroreticular resin (DIAION HP-20, 100 liters). The column was washed with water (400 liters) and 40% aqueous methanol solution (410 liters), successively, and then developed with 95% aqueous methanol solution (400 liters). The active fractions were combined and concentrated in vacuo to an aqueous concentrate. The wet mycelial cake obtained above (360 Kg) was suspended in methanol (300 liters) and extracted by stirring. This was repeated twice and the combined methanol extract (700 liters) was concentrated in vacuo. The two aqueous concentrates obtained from the HP-20 eluate and the mycelial cake extract were combined and further evaporated in vacuo (to 70 liters), and the activity in the concentrate was extracted twice with ethyl acetate (2×35 liters). The extract was concentrated in vacuo to dryness to leave an oily solid (1.03 Kg, 220 mcg./mg.), which was dissolved in a mixture of ethyl acetate and methanol (20:1, 2.2 liters) and applied to a column of active carbon (5 liters volume). The column was developed with the same solvent mixture, the active eluates were combined and concentrated in vacuo to give a dark brown solid, which was crystallized from hot methanol yielding a brownish yellow crystalline powder (279 g, 650 mcg./mg.).

The crystalline material thus obtained was a mixture of components A and B, whose separation was achieved by Diaion HP-20 chromatography. A portion of the mixture (100 g) was dissolved in 90% aqueous methanol and the solution was applied on a column of HP-20 resin (5 liters). The column was developed by 80% aqueous methanol to give two active fractions. From the concentrate of first active fraction (24 liters) were obtained pale yellow needle-like crystals of Bu-2313B (45 g) which were recrystallized twice from methanol to give an analytically pure preparation (32 g). The second active eluate (23 liters) was concentrated in vacuo to give a mixture of components A and B (ca. 20 g) which was separated by silica gel column chromatography developed by chloroform. Pure crystals of component A (4 g) were obtained, after recrystallization, from the fast moving fractions, and an additional amount of component B (7.5 g) was recovered from the latter part of the eluates.

Analyses of the pure crystalline products were as follows:

Bu-2313A - Calculated for $C_{27}H_{35}NO_9$: C, 62.65; H, 6.82; N, 2.71; O, 27.82. Found: C, 62.57; H, 6.64; N, 2.60; O, 28.20 (by difference).

Bu-2313B - Calculated for $C_{26}H_{33}NO_9$: C, 62.03; H, 6.56; N, 2.78; O, 28.63. Found: C, 61.77; H, 6.80; N, 2.65; O, 28.78 (by difference).

EXAMPLE 4

Preparation of A Crystalline Bromobenzene Solvate of Bu-2313B

Bu-2313B (100 mg) was dissolved in 4 ml of hot bromobenzene, to which petroleum ether was added dropwise until a slight turbidity was induced. The solution was allowed to stand overnight at room temperature to complete the crystallization. The bromobenzene solvate of Bu-2313B was obtained as yellow needles (80 mg), $[\alpha]_D^{21} = -51.2°$ (c 0.88, methanol). λ max in ethanol: 225, 295(sh), 352 and 369 nm. NMR spectrum: δ 7.1 ppm (5H) for bromobenzene.

Analysis: Calculated for $C_{32}H_{40}NO_{10}Br$ ($C_{26}H_{33}NO_9 \cdot C_6H_5Br \cdot H_2O$): C, 56.64; H, 5.90; N, 2.06; Br, 11.80; O, 23.60. Found: C, 56.87; H, 5.84; N, 2.19; Br, 12.10; O, 23.00 (by difference).

EXAMPLE 5

Preparation of the Sodium Salt of Bu-2313B

To a solution of 200 mg of Bu-2313B in 10 ml of methylene chloride was added 30 ml of water. To the solution was added, dropwise with stirring, 1 N NaOH, to pH 11.5. After stirring for 30 minutes, the solvent layer was separated and the aqueous layer was extracted twice with 30 ml each of n-butanol. The extracts were combined and concentrated in vacuo. The solid thus obtained was dissolved in a small amount of acetone and precipitated by the addition of n-hexane, to give 176 mg of Bu-2313B sodium salt. A part of this material (45 mg) was crystallized from a mixture of benzene-methanol to yield 36 mg of pale yellow crystals, melting at 236°–241° C. (decomp.), $[\alpha]_D^{23} = -7.4$ (c 0.94 methanol).

Analysis: Calculated for $C_{26}H_{32}NO_9Na \cdot H_2O$: C, 57.46; H, 6.26; N, 2.58; Na, 4.24; O, 29.46. Found: C, 57.57; H, 6.29; N, 2.39; Na, 4.21; O, 29.54 (by difference).

EXAMPLE 6

Preparation of the Sodium Salt of Bu-2313A

The general procedure of Example 5 is repeated except that the Bu-2313B utilized therein is replaced by an equal amount of Bu-2313B, and the sodium salt of Bu-2313A is thereby produced.

We claim:

1. A microbiological process for the preparation of a mixture of the antibiotics Bu-2313A and Bu-2313B which comprises cultivating a strain of *Micropolyspora caesia* having the identifying characteristics of A.T.C.C. 31295, 31296, 31297 or 31298 under submerged aerobic conditions in an aqueous culture medium containing assimilable sources of carbon and nitrogen until a substantial amount of said antibiotic mixture is produced by said microorganism in said culture medium.

2. The process of claim 1 which includes the additional step of recovering the antibiotic mixture from the culture medium.

3. The process of claim 2 in which the microorganism is *Micropolyspora caesia* A.T.C.C. 31298.

4. A microbiological process for the preparation of the antibiotic Bu-2313B which comprises
   (a) cultivating a strain of *Micropolyspora caesia* having the identifying characteristics of A.T.C.C. 31295, 31296, 31297 or 31298 under submerged aerobic conditions in an aqueous culture medium containing assimilable sources of carbon and nitrogen until a substantial amount of antibiotic activity is produced by said microorganism in said culture medium;
   (b) recovering the antibiotic mixture produced in step (a) from the culture medium; and
   (c) separating Bu-2313B from said antibiotic mixture by chromatography on a macroreticular polymer resin.

5. The process of claim 4 in which the microorganism is *Micropolyspora caesia* A.T.C.C. 31298.

6. A microbiological process for the preparation of the antibiotic Bu-2313A which comprises
   (a) cultivating a strain of *Micropolyspora caesia* having the identifying characteristics of A.T.C.C. 31295, 31296, 31297 or 31298 under submerged aerobic conditions in an aqueous culture medium containing assimilable source of carbon and nitrogen until a substantial amount of antibiotic activity is produced by said microorganism in said culture medium;
   (b) recovering the antibiotic mixture produced in step (a) from the culture medium;
   (c) separating the major portion of Bu-2313B from said antibiotic mixture by chromatography on a macroreticular polymer resin; and
   (d) separating Bu-2313A from the residual Bu-2313B by chromatography on silica gel.

7. The process of claim 6 in which the microorganism is *Micropolyspora caesia* A.T.C.C. 31298.

* * * * *